United States Patent [19]

King et al.

[11] Patent Number: 5,288,991
[45] Date of Patent: Feb. 22, 1994

[54] OPTICAL SYSTEM FOR RAPID INSPECTION OF VIA LOCATION

[75] Inventors: Mark R. King, Milton; William H. Vonderhaar, Newburgh, both of N.Y.

[73] Assignee: International Business Machines Corporation, Armonk, N.Y.

[21] Appl. No.: 985,390

[22] Filed: Dec. 4, 1992

[51] Int. Cl.$^5$ .......................... G02B 6/04; G02B 27/00
[52] U.S. Cl. ................................ 250/216; 250/227.28
[58] Field of Search ........... 250/216, 225, 226, 227.11, 250/227.2, 227.26, 227.28, 227.32, 562, 563, 571, 572; 356/376, 380, 429, 430

[56] References Cited

U.S. PATENT DOCUMENTS

| | | | |
|---|---|---|---|
| 3,933,556 | 1/1976 | Strack et al. ......................... | 156/155 |
| 4,222,630 | 9/1980 | Delignieres ................. | 250/227.26 X |
| 4,787,013 | 11/1988 | Sugino et al. ......................... | 362/32 |
| 4,812,614 | 3/1989 | Wang et al. ..................... | 219/124.34 |
| 4,939,630 | 7/1990 | Kikuchi et al. ....................... | 362/268 |
| 4,952,022 | 8/1990 | Genovese ......................... | 350/96.24 |
| 4,974,927 | 12/1990 | Kimura .............................. | 350/96.24 |
| 5,109,459 | 4/1992 | Eibert et al. ................ | 250/227.26 X |
| 5,117,245 | 5/1992 | Gordon ....................... | 250/227.26 X |

FOREIGN PATENT DOCUMENTS 197811 11/1978 France .

Primary Examiner—David C. Nelms
Assistant Examiner—John R. Lee
Attorney, Agent, or Firm—Whitham & Marhoefer

[57] ABSTRACT

An inspection system in which the surface of a substrate is continuously scanned by a linear CCD. The surface is illuminated in a narrowly focused strip from a broadband light source that is selectively wavelength filtered to optimize image contrast to the optical characteristics of the surface under inspection. A channel integrator in the light source optical system provides illumination homogeneity at the surface of the substrate.

10 Claims, 2 Drawing Sheets

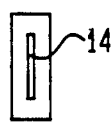  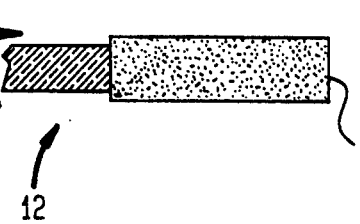 
FIG. 2C   FIG. 2A   FIG. 2B
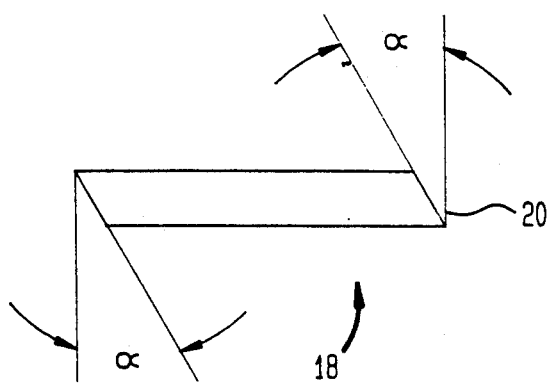 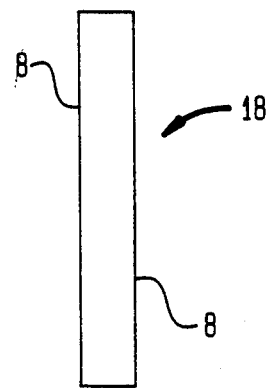
FIG. 3A   FIG. 3B
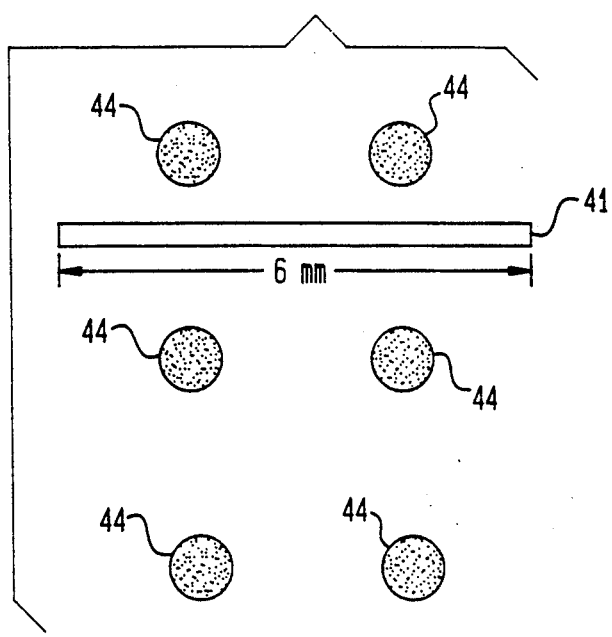 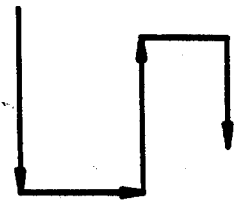
FIG. 4A   FIG. 4B

OPTICAL SYSTEM FOR RAPID INSPECTION OF VIA LOCATION

BACKGROUND OF THE INVENTION

1. Field of the Invention

This invention relates to an optical inspection system and more particularly to an improved system for rapidly determining the location and size of via openings in substrate sheets.

2. Description of the Prior Art

As will be appreciated by those skilled in the art, via openings are formed in ceramic substrate sheets in order to provide connecting paths through the sheets. A number of sheets are used to form a multi-layer module that mechanically supports and electrically interconnects a plurality of integrated circuit chips mounted on the module. The via openings are very small and are usually closely spaced (e.g., 100 microns in diameter and 600 microns spacing). The ceramic substrates are sintered after the vias are formed. This sintering process can sometimes cause a change in the location of a via from its intended location; the difference between the intended location and the actual location is called distortion. For the next generation of substrates, which utilize a thin-film process, this distortion can affect the via locations; thereby preventing a satisfactory electrical connection between the via conductor and the thin-film wiring. It can also affect the electrical connection between two or more substrate sheets.

There are several prior art systems commercially available for measuring via distortion. They use an area array CCD detector and accompanying optics to illuminate the surface of the ceramic substrate and reflect light from the surface to the area array. A typical system of this type moves the substrate (under servo control) to a series of programmed positions relative to CCD area array. An image of a via is acquired by the CCD area array while the substrate is stationary. Because of the time required to position the substrate and to form the via image in prior art inspection systems, vias are inspected for distortion on a sampling basis only; usually only about one percent of the vias are inspected. Inspection by continuous scanning of the substrate surface has heretofore not been possible because of inadequate light available at the scanned surface to provide sufficient contrast between the via opening and the surface itself, and because an area CCD array is unsuited to continuous scanning.

SUMMARY OF THE INVENTION

A purpose of this invention is the provision of a via inspection system that can inspect via openings on a real-time basis; one-hundred-percent inspection in the time it takes the prior art system to inspect one percent of the vias.

Another purpose of the invention is the provision of a continuous scanning system that has an illumination source that can provide image contrast matched to the optical characteristics of the part under inspection.

Briefly, this invention contemplates the provision of an inspection system in which the surface of the substrate is continuously scanned by a linear CCD. The surface is illuminated in a narrowly focused strip from a broad-band light source that is selectively filtered to optimize image contrast to the optical characteristics of the surface under inspection. A channel integrator in the light source optics provides illumination homogeneity at the surface of the substrate.

BRIEF DESCRIPTION OF THE DRAWINGS

The foregoing and other objects, aspects and advantages will be better understood from the following detailed description of a preferred embodiment of the invention with reference to the drawings, in which:

FIGS. 2A, 2B, and 2C illustrate a fiber optic bundle component of the system illustrated in FIG. 1.

FIGS. 3A and 3B illustrate respectively a top and side view of a channel integrator component of the system illustrated in FIG. 1.

FIGS. 4A and 4B show respectively a representation of several vias under inspection and an inspection path.

DETAILED DESCRIPTION OF A PREFERRED EMBODIMENT OF THE INVENTION

Figure 1:
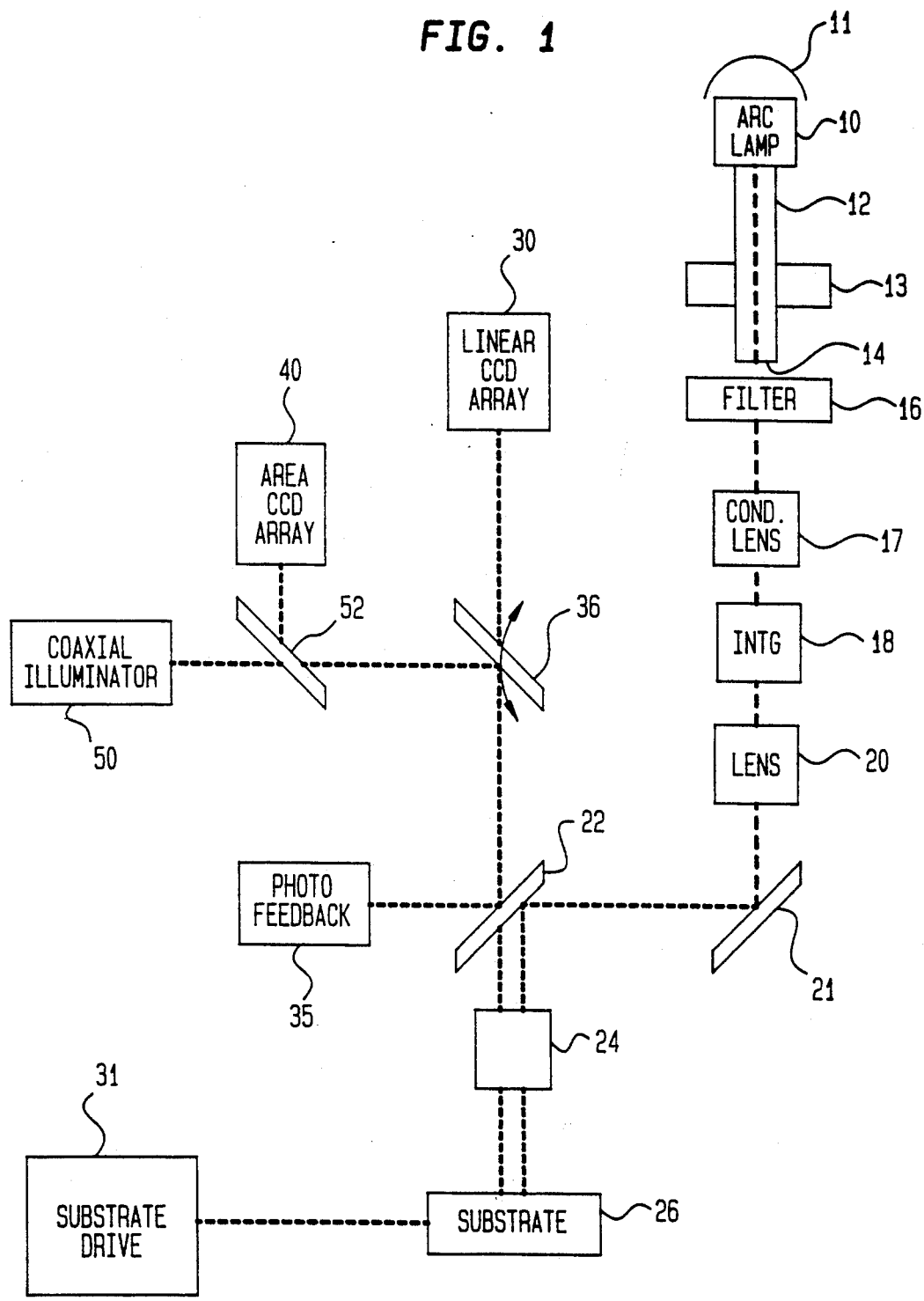
FIG. 1 is a schematic view of a optical inspection system in accordance with the teachings of this invention.

Referring now to FIG. 1, the arc of an Hg-Xe lamp 10 is focused by an elliptical housing 11 at the entrance pupil of a coaxial fiber optic bundle 12, which is preferably a circular to rectangular bundle, shown in more detail in FIG. 2. The coaxial fiber bundle 12 is advantageously movably mounted by support 13 so that to allow X, Y, and theta correction to ensure alignment of the illuminated strip image with a linear CCD array 30.

The light from the rectangular exit face 14 of the coaxial fiber bundle 12 is directed through a filter wheel 16 that is programmable and can accommodate a variety of filters, including neutral density, wavelength, and polarizing filters. It will be appreciated that the arc lamp 10 is a broad band light source, and is incoherent. A filter is selected to provide a near monochromatic illumination that maximizes the contrast of the via image with respect to the surface of the substrate surface 26.

Light from the rectangular exit face 14 of the coaxial fiber bundle 12, after passing through the filter wheel 16, is reimaged by a condenser lens 17 (at unity magnification) onto the entrance pupil of a channel integrator 18, shown in more detail in FIG. 3. The channel integrator 18 homogenizes the light from the end of the circular to rectangular bundle 12 so that the illuminated strip has a uniform intensity throughout the entire illuminated area.

A reimaging lens 20 relays the image of the exit face of the channel integrator 18 and a turning mirror 21 folds the light onto a beam splitter 22. The beam splitter 22 typically directs eighty percent of the incident light toward an imaging or objective lens 24 projecting an image of the exit face of the channel integrator 18 (e.g., approximately 0.1 mm by 6.0 mm) onto the part 26, which is under inspection; which is typically a substrate. This strip of light provides a scanning input illumination to a linear CCD array 30. An image of the part 26 under inspection is acquired by moving the part 26 in a serpentine fashion (using drive 31) with respect to the strip illuminated on the substrate 26.

The objective lens 24 reimages the light reflected from the surface of the substrate 26 to the linear CCD array 30 at a magnification to obtain a pixel size at the substrate surface sufficiently small to resolve via opening edge location (for example, a 6.5 times magnification to provide a two micron pixel size at the substrate surface).

A suitable photo-feedback detector 35 is preferably used to provide illumination intensity feedback to stabilize the output of the arc lamp 10 so as to minimize the effects of bulb aging and power supply variation.

A mirror 36 pivots to direct the image to either the linear CCD array 30 under measurement conditions, or to an area CCD array 40 for image observation. The system operation does not require simultaneous use of the video and scanning arrays and the pivoting mirror allows selection of either array.

FIGS. 2A, 2B, and 2C show the preferred embodiment of the circular to rectangular fiber bundle 12 shown in a side elevation in FIG. 2A. The input face (FIG. 2B) consists of a circular bundle 9, and the output face 14 consists of a rectangular section shown in FIG. 2C. The preferred material of this fiber is high grade optical fused silica.

FIGS. 3A and 3B show respectively a top view and a side view of the light homogenizer, or channel integrator 18. It consists of a piece of optical grade fused silica, with a 5 degree wedge angle $\alpha$ at the entrance face 20. This angle is used in place of the prior art anti-reflection coating, which would be damaged by the high intensity of the arc lamp 10 of FIG. 1. Typical dimensions of the channel integrator are 22 mm long, by 11.5 mm wide. The sides 8 of the channel integrator are held parallel to a high tolerance.

FIG. 4A shows the illuminated strip 41 on the surface of the substrate 26, and FIG. 4B shows the direction of table scan relative to this illuminated strip. The image is acquired in real time by scanning the part under inspection 26 in a serpentine fashion as shown in FIG. 4B. The via images 44 are formed by a combination of table motion in one direction, and electronic scanning of the pixels of the linear CCD array in a direction orthogonal to this. Note that this differs from prior art systems in that an image is acquired in two dimensions, without the need for an area array type CCD detector. The pixel data is sent to an analog to digital converter, and then to an image processor.

An additional coaxial illuminator 50 is provided to illuminate the surface when the area array 40 is used. Its light passes through a video beam splitter 52, reflects from the mirror 36, and is directed to the surface under inspection with its angle of incidence normal to the surface. An objective lens 24 reimages the illuminated area and projects it onto the are array 40. The area array is mounted to provide independent focus for the image to insure simultaneous focus of the measured image (linear CCD array 30) and the observed image (area CCD array 40). The linear array 30 and the area array 40 thus see identical images. Note that the linear array 30 is used for distortion measurement, whereas the area array 40 is used for observation of the image.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. An optical system for illuminating a narrow rectangular area of a surface of a part to image features of said part on a linear CCD array as said part moves relative to the narrow rectangular area and said linear CCD array, said optical system comprising in combination in an optical path:
    a broad band, non-coherent light source;
    a fiber optic bundle having an entrance pupil and an exit pupil;
    means to direct light from said broad band, non-coherent light source to said entrance pupil of said fiber optic bundle;
    means to direct light from said exit pupil of said fiber bundle to a filter having a selectable filter element that provides enhanced contrast between a via image and said surface;
    a channel integrator for providing illumination homogenization, said channel integrator having an entrance face and an exit face;
    means to image said exit pupil of said fiber bundle, passing through said selectable filter, onto the entrance face of said channel integrator;
    means including a beam splitter to image the exit face of said channel integrator onto said surface, and;
    means including said beam splitter to image light reflected from said surface on said linear CCD array.

2. An optical system for illuminating a narrow rectangular area of a surface of a part to image features of said part as in claim 1, wherein said selectable filter element is wavelength selectable.

3. An optical system for illuminating a narrow rectangular area of a surface of a part to image features on said part as in claim 1, wherein the selectable filter element includes a neutral density filter.

4. An optical system for illuminating a narrow rectangular area of a surface of a part to image features as in claim 1, wherein said broad band, non-coherent light source is a mercury-xenon arc lamp.

5. An optical system for illuminating a narrow rectangular area of a surface of a part to image features on said part as in claim 1, wherein the selectable filter element includes a polarizing filter.

6. An optical system for illuminating a narrow rectangular area of a surface of a part to image features on said part as in claim 2, wherein the selectable filter element includes a neutral density filter.

7. An optical system for illuminating a narrow rectangular area of a surface of a part to image features as in claim 2, wherein said broad band, non-coherent light source is a mercury-xenon arc lamp.

8. An optical system for illuminating a narrow rectangular area of a surface of a part as in claim 1, wherein said fiber optic bundle has a circular entrance pupil and rectangular exit pupil.

9. A method for illuminating a narrow rectangular area of a surface of a part to image features of said part on a linear CCD array as said part moves relative to the narrow rectangular area and said linear CCD array, said method comprising the steps of:
    directing light from a broad band, non-coherent light source to an entrance pupil of a fiber optic bundle;
    directing light from an exit pupil of said fiber bundle to a filter having a selectable filter element that provides enhanced contrast between a via image and said surface;
    imaging an exit pupil of said fiber bundle, passing through said selectable filter element onto an entrance face of a channel integrator;
    imaging an exit face of said channel integrator onto said surface, and;
    imaging light reflected from said surface on said linear CCD array.

10. A method for illuminating a narrow rectangular area of a surface of a part to image features of said part on a linear CCD array as in claim 9, wherein said fiber optic bundle has a circular entrance pupil and rectangular exit pupil.

* * * * *